United States Patent [19]

Pesson et al.

[11] 4,125,720
[45] Nov. 14, 1978

[54] PROCESS FOR THE PREPARATION OF 4-CHLORO-5-ALKOXYCARBONYL-2-METHOXY-PYRIMIDINES

[75] Inventors: Marcel E. Pesson, Paris; Suzanne W. Geiger, Montmorency, both of France

[73] Assignee: Laboratoire Roger Bellon, France

[21] Appl. No.: 786,777

[22] Filed: Apr. 12, 1977

[30] Foreign Application Priority Data

Apr. 16, 1976 [FR] France ............................. 76 11448

[51] Int. Cl.$^2$ ............................................ C07D 239/24
[52] U.S. Cl. .................................... 544/318; 544/279; 544/317; 544/330; 544/326; 544/314
[58] Field of Search ...................................... 260/251 R

[56] References Cited

U.S. PATENT DOCUMENTS

| | | | |
|---|---|---|---|
| 1,766,748 | 6/1930 | Hilger | 260/251 R |
| 2,238,638 | 3/1941 | Hromaika | 260/251 R |
| 2,948,725 | 8/1960 | Duschinsky et al. | 260/251 R |
| 3,758,472 | 9/1973 | Bowden | 260/251 R |
| 3,798,220 | 3/1974 | Klemm et al. | 260/251 R |
| 4,052,397 | 10/1977 | Blackwell et al. | 260/251 R |

*Primary Examiner*—Nicholas S. Rizzo

[57] ABSTRACT

Process for the preparation of a 4-chloro-5-alkoxycarbonyl-2-methoxy-pyrimidine of the formula:

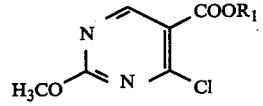

in which $R_1$ is a lower alkyl radical with 1 to 4 carbon atoms, which comprises the following stages:

A) condensation of a salt of O-methylisourea and an inorganic or organic acid, with an alkyl alkoxymethylenemalonate

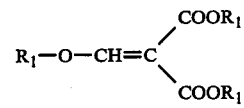

in an aqueous medium and in the presence of an excess of an alkali metal hydroxide, to form the corresponding salt of the 5-alkoxycarbonyl-4-hydroxy-2-methoxy-pyrimidine, and neutralization of the said salt by the addition of an inorganic or organic acid, in order to liberate this 5-alkoxycarbonyl-4-hydroxy-2-methoxy-pyrimidine, and

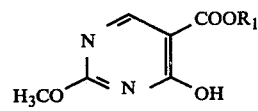

B) bringing the latter compound, suspended in dimethylformamide, into contact with thionyl chloride, at room temperature, in order to form the corresponding 4-chloro-5-alkoxycarbonyl-2-methoxy-pyrimidine:

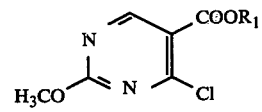

4 Claims, No Drawings

PROCESS FOR THE PREPARATION OF 4-CHLORO-5-ALKOXYCARBONYL-2-METHOXY-PYRIMIDINES

Application to the preparation of 6-ethoxycarbonyl-8-ethyl-2-methoxy-5-oxo-5,8-dihydro-pyrido[2,3-d]pyrimidine.

6-Ethoxycarbonyl-8-ethyl-2-methoxy-5-oxo-5,8-dihydro-pyrido[2,3-d]pyrimidine (I)

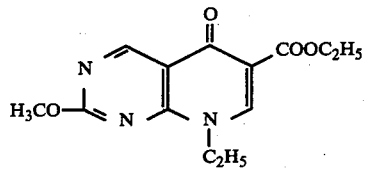

and the corresponding acid are synthesis intermediates which can be used especially for the preparation of pyromidic acid ($II_a$) and pipemidic acid ($II_b$), which are synthetic antibacterial agents:

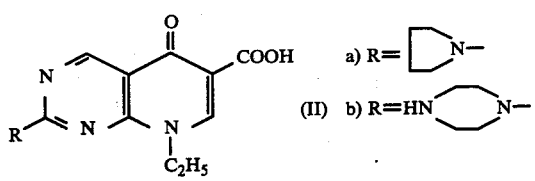

In the present state of the art, the use of 6-ethoxy-carbonyl-8-ethyl-2-methoxy-5-oxo-5,8-dihydro-pyrido[2,3-d]-pyrimidine (I) or of the corresponding acid for the industrial preparation of compounds ($II_a$) and ($II_b$) is of little economic interest, since the known processes for the preparation of (I) only allow this substance to be obtained with mediocre yields.

In effect, only two methods are known at present for preparing 6-ethoxycarbonyl-8-ethyl-2-methoxy-5-oxo-5,8-dihydro-pryido[2,3-d]pyrimidine (I).

First Method

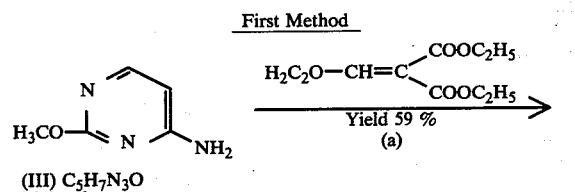

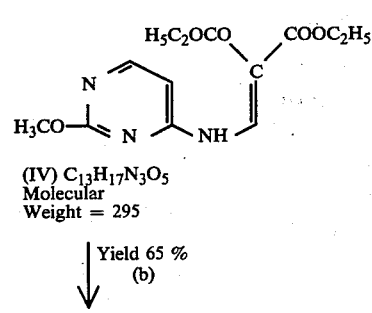

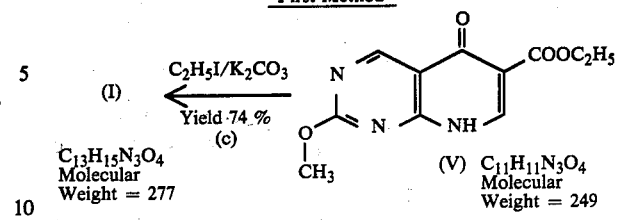

According to the first method, the starting material, which is 4-amino-2-methoxy-primidine (III), is condensed with ethyl ethoxymethylenemalonate [stage (a)] to give the 4-pyrimidyl-aminomethylenemalonic diester (IV) with a yield of 59%. Heat cyclisation of this diester [stage (b)] leads to 6-ethoxycarbonyl-5-oxo-2-methoxy-5,8-dihydro-pyrido[2,3-d]-pyrimidine (V) with a yield of 65%. Alkylation of (V) with methyl iodide [stage (c)]gives the ester (I) with a yield of 74%. These operations taken together result in the ester (I) with an overall yield of the order of 30%, calculated starting from 4-amino-2-methoxy-pyrimidine (III).

In addition to this yield being itself poor, account must be taken of the difficulties of preparing the starting material (III).

In effect, 4-amino-2-methoxy-pyrimidine (III) can only conveniently be prepared by two processes, namely (a) and (b).

Process a

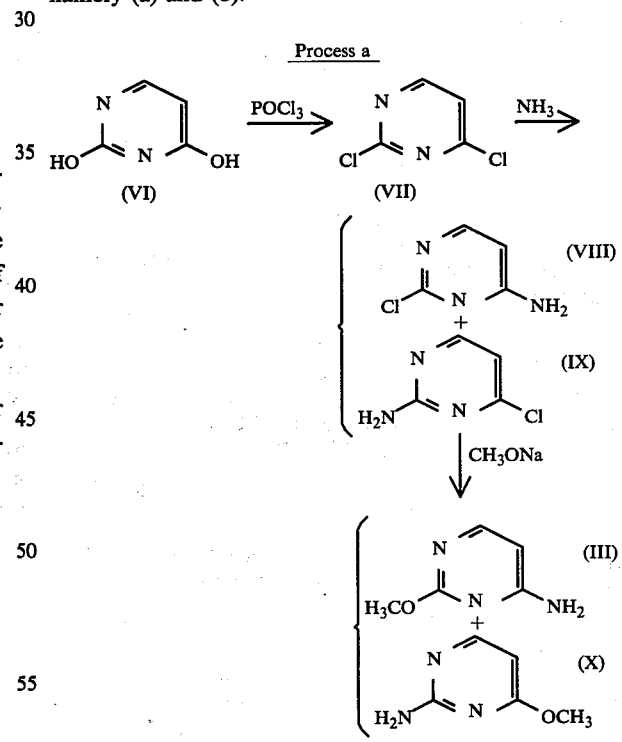

According to process (a) the starting material, which is uracil (VI), is treated with phosphorus oxychloride to give 2,4-dichloro-pyrimidine (yield 80–90%); this compound gives a mixture of 4-amino-2-chloro-pyrimidine (VIII) and 2-amino-4-chloro-pyrimidine (IX) on treatment with ammonia. This mixture, when treated with sodium methylate, gives a mixture of the two corresponding methoxy derivatives, from which 4-amino-2-methoxy-pyrimidine (III) can be isolated with a yield, calculated on the dichloro derivative, varying between 40% [G. E. HILBERT and T. B. JOHNSON J. Am. Chem. Soc. 52, 1152–1157 (1930)] and 60% [KARLINSKAYA and K. BORISON Zhur Obshchei Khim 27, 2113–2114 (1957) – C.A. 51, 7.379 f].

The preparation of 6-ethoxycarbonyl-8-ethyl-2-methoxy-5-oxo-5,8-dihydro-pyrido[2,3-d]pyrimidine, starting from 4-amino-2-methoxy-pyrimidine prepared according to process (a) indicated above, thus cannot give an overall yield greater than 15% relative to the starting uracil. Moreover, this overall process thus necessitates seven stages.

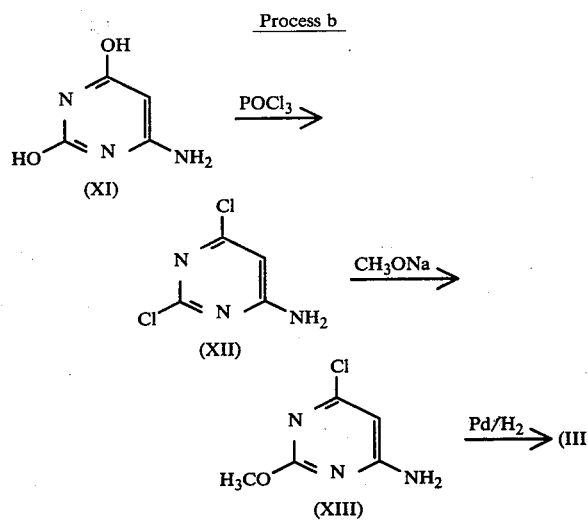

According to process (b) for the preparation of 4-amino-2-methoxy-pyrimidine (III), the starting material is 4-amino-2,6-dihydroxy-pyrimidine (XI) which, when treated with phosphorus oxychloride, gives 4-amino-2,6-dichloro-pyrimidine (XII) which, when treated with sodium methylate, gives 4-amino-6-chloro-2-methoxy-pyrimidine (XIII); this compound, in turn, is reduced by hydrogen, in the presence of palladium, to give 4-amino-2-methoxy-pyrimidine (III).

The overall yield for the two opertions varies between 35% [G. SPITELLER and M. BRETSCHNEIDER, Monatshefte fur Chemie 32, 183–192 (1961)] and 51.5% [W. KLOETZER and J. SCHANT, Monatshefte fur Chemie 94, 1178–1189 (1963)].

Thus, starting from 4-amino-2-methoxy-pyrimidine prepared by this process (b), the preparation of 6-ethoxycarbonyl-8-ethyl-2-methoxy-5-oxo-5,8-dihydro-pyrido[2,3-d]-pyrimidine necessitates six stages and the overall yield, calculated on (XI), does not exceed 15%.

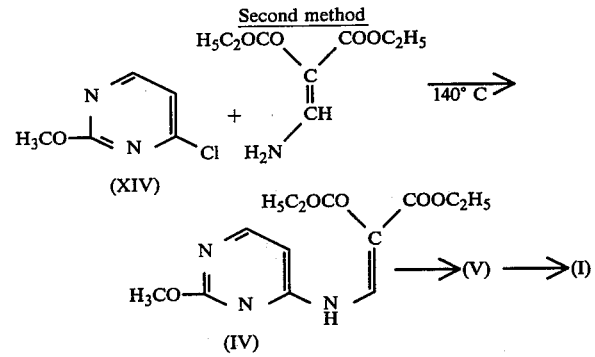

Morever, the second method which is known for the preparation of 6-ethoxycarbonyl-8-ethyl-2-methoxy-5-oxo-5,8-dihydro-pyrido [2,3-d]pyrimidine (I) is a variant of the first method; according to this variant, 4-chloro-2-methoxy-pyrimidine (XIV) is heated at 140° C, under pressure, with an excess of ethyl aminomethylenemalonate, which give ethyl N-(2-methoxy-4-pyrimidyl-aminomethylenemalonate (IV). The subsequent operations are identical to those of the first method.

This variant is not described in the literature and 4-chloro-2-methoxy-pyrimidine (XIV) which, in principle, is used in this reaction, is only mentioned in a Russian article summarised in Chemical Abstracts of 1974 [O. P. SHKRUKO; S. G. BARAM; V. P. MAMAEV Izv. Sib. Otd. Akad. Nauk, S.S.R. Khim. Nauk, 1973, 81-85 – C. A. 1974, 80, 59,913e].

This is certainly a product which is not easily accessible.

The present invention therefore relates to a new process for the preparation of 6-ethoxycarbonyl-8-ethyl-2-methoxy-5-oxo-5,8-dihydro-pyrido[2,3-d]pyrimidine which makes it possible to obtain a high yield, consistent with an industrial preparation process which is of economic value.

The process according to the invention for the preparation of 6-ethoxycarbonyl-8-ethyl-2-methoxy-5-oxo-5,8-dihydro-pyrido[2,3-d]pyrimidine comprises five stages.

In the first stage (A), a salt of O-methylisourea with an inorganic or organic acid is used as the starting material; the use of the neutral sulphate of O-methylisourea (XV), an industrial product which is easily accessible, is particularly desirable. Condensation of this salt with ethyl ethoxymethylenemalonate, in the presence of an excess of an alkali metal hydroxide, gives the corresponding salt of 5-ethoxycarbonyl-4-hydroxy-2-methoxy-pyrimidine (XVI), which is liberated by neutralisation with an inorganic or organic acid, preferably acetic acid.

In the second stage (B), treating 5-ethoxycarbonyl-4-hydroxy-2-methoxy-pyrimidine with a suitable agent gives 4-chloro-5-ethoxycarbonyl-2-methoxy-pyrimidine (XVII) where the halogen atom is very reactive.

In the third stage (C), reacting the last compound (XVII) with ethyl N-ethyl-β-aminopropionate gives 4-(N-ethyl-N-β-ethoxycarbonylethyl)-amino- 5-ethoxycarbonyl-2-methoxy-pyrimidine (XVIII).

In the fourth stage (D), cyclisation of this compound with an alkali metal alcoholate, according to the method described by DIECKMANN, gives 6-ethoxycarbonyl-8-ethyl-2-methoxy-5-oxo-5,6,7,8-tetrahydro-pyrido[2,3-d]pyrimidine (XIX).

In the fifth stage (E), the latter compound is dehydrogenated to 6-ethoxycarbonyl-8-ethyl-2-methoxy-5-oxo-5,8-dihydro-pyrido[2,3-d]pyrimidine (I):

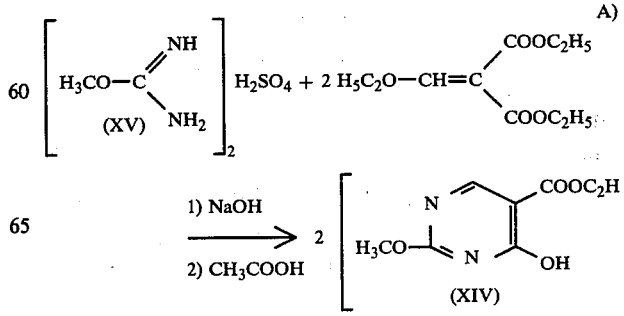

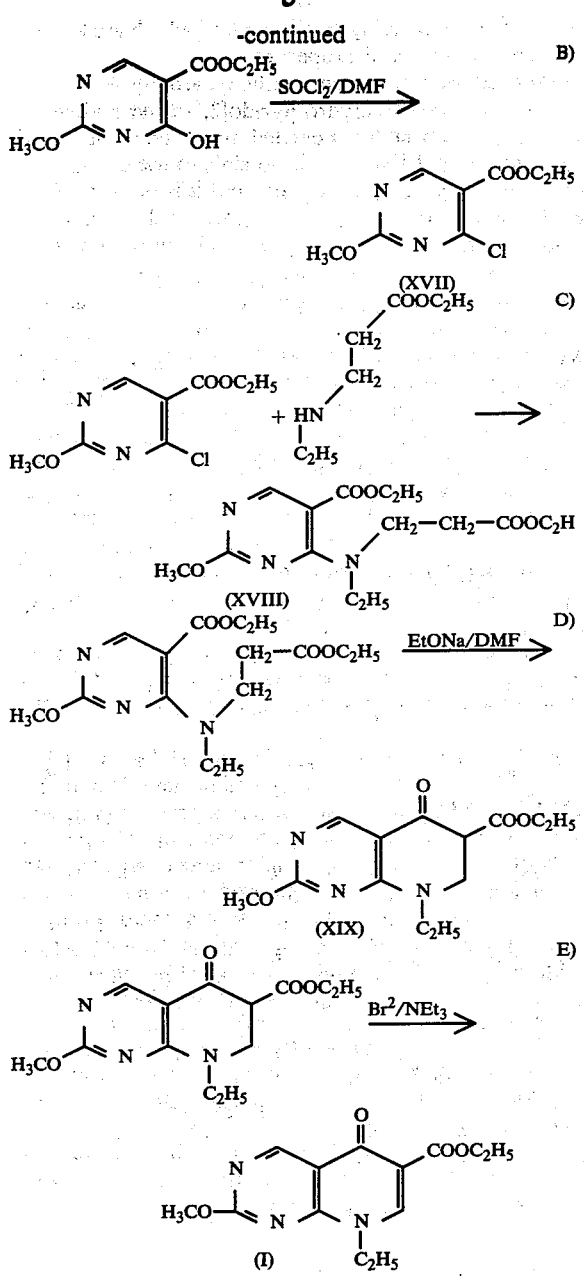

The intermediate products are obtained, in the various stages, with yields of between 75 and 95%, so that the overall yield for the preparation of (I) is between 60 and 65%.

Stage A

The condensation of the neutral sulphate of O-methylisourea with ethyl ethoxymethylenemalonate has already been studied [H. KOPPEL, R. SPRINGER, R. ROBINS and C. C. CHENG J. Org. Chem. 27, 3614–3617 (1962)]. However, under the conditions indicated by the authors mentioned, who operate in an anhydrous medium, in methanol and in the presence of sodium methylate, the main reaction is complicated by a transesterification reaction which, at the end of the operation, gives the methyl ester instead of the ethyl ester (XVI). The yield is mediocre (31%).

The applicant company has found that the operation can more advantageously be carried out in water: an aqueous solution of 1 mol of the neutral sulphate of O-methylisourea (concentration of between 5 and 10%) has the corresponding amount (2 mols) of ethyl ethoxymethylenemalonate added thereto, and the mixture is stirred vigorously so as to keep the second reagent emulsified. An aqueous solution of an alkali metal hydroxide is then added thereto at a rate such that the temperature of the mixture remains between 20° and 30° C. The mixture is stirred for another two hours at room temperature, after the addition of the alkaline reagent. If sodium hydroxide solution is used as the reagent, the sodium salt of the ester (XVI) precipitates in the medium which is brought to pH 5 by the addition of an inorganic or organic acid when the reaction has finished. The solution obtained, which is filtered if necessary in order to remove a small amount of insoluble matter, is extracted with an appropriate solvent chosen, preferably, from the polyhalogenated aliphatic hydrocarbons, more especially chloroform. After washing and drying the organic solution, evaporation in vacuo leaves 5-ethoxycarbonyl-4-hydroxy-2-methoxy-pyrimidine (XVI), which is practically pure, with a yield of about 80%. The product can then be purified by recrystallisation from a suitable solvent, especially isopropanol.

Stage B

Conversion of the 4-hydroxy derivative (XVI) to the corresponding 4-chloro compound (XVII) is a conventional operation for the pyrimidine series. A fairly large variety of processes exists for carrying out such a conversion process. In general, heating of the hydroxy-compound with phosphorus oxychloride, alone or in the presence of basic catalysts such as dimethylaniline, diethylaniline or triethylamine, is used. Mixtures of phosphorus oxychloride and phosphorus pentachloride are also sometimes used and the reactions can optionally be carried out at high temperature, using a sealed tube.

In the case of the compound (XVI), these various methods cannot be applied, either because they give yields which are too low for industrial use, or because they lead to complex by-products, or because they do not make the reaction possible (recovery of the starting material or of its hydrolysis products, after the usual treatments for such a reaction).

According to one characteristic of the invention, 4-chloro-5-ethoxycarbonyl-2-methoxy-pyrimidine (XVII) can be obtained easily, starting from the corresponding 4-hydroxy compound (XVI), by treating, at room temperature, a suspension of the latter compound in D.M.F. (dimethylformamide) with thionyl chloride.

It is preferable to start from a concentrated suspension obtained, for example, by stirring one part by weight of the compound (XVI) in about 2 volumes of D.M.F. The thionyl chloride, which can be used in the ratio of one molecule per molecule of hydroxy-derivative, is added rapidly thereto; however, to ensure a complete and rapid reaction, it is preferable to use an excess of this reagent, for example 1.5 mols. The reaction is exothermic and the derivative (XVI) passes into solution. The reaction is left to finish at room temperature for 30 minutes to one hour.

The reaction mixture is poured onto iced water and the reaction product is isolated by extraction using a suitable solvent which can be chosen, especially, from amongst the polyhalogenated hydrocarbons or the lower aromatic hydrocarbons, such as benzene or toluene. After washing with water and drying, evaporation of the organic solutions leaves the chlorinated derivative (XVII) in the form of an oil which can, optionally, be purified by distillation under a high vacuum. The oil then crystallises. Melting point 28°–29° C. The yield for the conversion (XVI)→(XVII), under these conditions, is about 95%.

Stage C

The reaction between the chlorinated derivative (XVII) and ethyl N-ethyl-β-aminopropionate is carried out starting from equimolecular quantities of the two reagents, in the presence of an acceptor, used in a slight excess, for the hydracid which is formed in the reaction. Inorganic or organic acceptors may be used. The reaction is preferably carried out in a solvent such as a polyhalogenated or aromatic hydrocarbon, preferably benzene, in the presence of triethylamine. The reaction is completed by heating at 50° C for 1 to 2 hours.

The diester (XVIII) is isolated, with a theoretical yield, according to the usual processes. It is in the form of an oil which cannot be distilled without decomposition and it is used immediately for the following operation.

Stage D

Cyclisation of the diester (XVIII) can be carried out using potassium tert.-butylate in an organic solvent. However, it has been found that it is technically more advantageous to carry out the reaction with sodium ethylate in solution in D.M.F. A slight excess of this alkaline agen (1.1 mol per mol of diester employed) is used.

It is desirable to use an ethylate which has been freshly prepared by dissolving the corresponding quantity of sodium in ethanol, and then evaporating off the excess of the ethanol. The ethylate is dissolved in a volume of D.M. F. such that the ethylate concentration is between 15 and 20%. The diester (XVIII), diluted with its own volume of D.M.F., is added to the ethylate solution at a rate such that the temperature of the reaction mixture remains between 15° and 25° C. After stirring at room temperature for 1 to 2 hours, the reaction is completed by heating for 1 hour at 50° C in vacuo, in order to remove the ethanol which is formed in the reaction. After cooling, the solution is neutralised by the addition of the calculated quantity of an inorganic or organic acid, preferably acetic acid. 6-Ethoxycarbonyl-8-ethyl-2-methoxy-5-oxo-5,6,7,8-tetrahydro-pyrido[2,3-d]pyrimidine (XIX) which precipitates is filtered off, washed with water and recrystallised from a suitable solvent. It is obtained with a yield of between 80 and 90%.

Stage E

Conversion of the tetrahydro-derivative (XIX) to 6-ethoxycarbonyl-8-ethyl-2-methoxy-5-oxo-5,8-dihydro-pyrido[2,3-d]pyrimidine by the successive action of bromine and of a tertiary amine is carried out, according to the principle described previously, by effecting halogenation in a polyhalogenated aliphatic hydrocarbon, preferably chloroform. Dehydrohalogenation is preferably carried out in an alcoholic medium.

6-Ethoxycarbonyl-8-ethyl-2-methoxy-5-oxo-5,8-dihydro-pyrido[2,3-d]pyrimidine is characterised by the reactivity of the methoxy group towards nucleophilic reagents, in particular towards secondary amines. The products thus obtained can be saponified thereafter and give the corresponding acids, some of which are known for their antibacterial properties.

The reaction between 6-ethoxycarbonyl-8-ethyl-2-methoxy-5-oxo-5,8-dihydro-pyrido[2,3-d]pyrimidine and a secondary amine is carried out at temperatures of between 50° and 100° C. It is possible to use equimolecular proportions of the reagents, but it is often preferable to employ an excess (2 to 5 mols) of the secondary amine, in particular if this compound can be easily removed at the end of the reaction. It is possible to operate in the absence of a solvent, by heating, at a suitable temperature, the mixture of the two reagents, which have been homogenised by stirring. It is also possible to carry out the reaction in a solvent with a boiling point equal to or greater than the desired reaction temperature. Lower alcohols, aromatic hydrocarbons, lower acid dialkylamides, such as D.M.F. or dimethylacetamide, can be used as solvents. It is also possible to use dimethylsulphoxide, but the use of this compound is to be avoided, because of the odour which is imparted to the products by by-products from the decomposition of the dimethylsulphoxide under the conditions of the reaction.

Example 3 illustrates a typical reaction of this type with pyrrolidine. The ester which is obtained gives, after saponification, pyromidic acid (II$_a$), with excellent yields.

A particularly valuable application of the ester (I) is its use for the preparation of pipemidic acid (II$_b$) by the action of an excess (3 mols) of piperazine hexahydrate, in the absence of a solvent, at a temperature of 80° C, as is described in the example. Under these conditions, the formation of the disubstitution product of piperazine is greatly reduced. Saponificaion of the crude product from the reaction, followed by acidificaion with acetic acid, gives pipemidic acid which, after purification, is obtained with a yield of between 80 and 90%.

The present invention also relates to a process for the preparation of 4-chloro-5-ethoxycarbonyl-2-methoxy-pyrimidine which is the intermediate product which is of value in the synthesis of 6-ethoxycarbonyl-8-ethyl-2-methoxy-5-oxo-5,8-dihydro-pyrido[2,3-d]pyrimidine; in general terms, the subject of the invention is a process for the preparation of 4-chloro-5-alkoxycarbonyl-2-methoxy-pyrimidines of the formula:

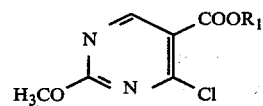

in which R$_1$ is a lower alkyl radical with 1 to 4 carbon atoms; such a process comprises the two following stages:

(A) condensation of a salt of O-methylisourea and of an inorganic or organic acid, with an alkyl alkoxymethylenemalonate of the formula:

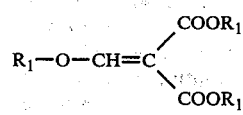

in which R$_1$ is defined as above, in an aqueous medium, in the presence of an excess of an alkali metal hydroxide, to form the corresponding salt of a 5-alkoxycarbonyl-4-hydroxy-2-methoxy-pyrimidine, followed by neutralisation of the said salt by the addition of an inorganic or organic acid, in order to liberate this 5-alkoxycarbonyl-4-hydroxy-2-methoxy-pyrimidine of the formula:

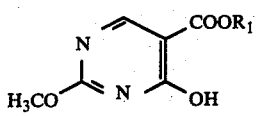

in which $R_1$ is defined as above, and (B) bringing this compound, suspended in dimethylformamide, into contact with thionyl chloride, at room temperature, in order to form the corresponding 4-chloro-5-alkoxycarbonyl-2-methoxy-pyrimidine:

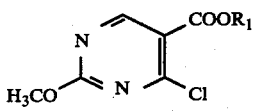

More particularly, the process for the preparation of 4-chloro-5-ethoxycarbonyl-2-methoxy-pyrimidine comprises the following stages:

(A) the condensation of a salt of O-methylisourea and of an inorganic acid, with ethyl ethoxymethylenemalonate, in an aqueous medium, in the presence of an excess of an alkali metal hydroxide, followed by neutralisation of the salt formed by the addition of an inorganic or organic acid in order to liberate the 4-chloro-5-ethoxycarbonyl- 2-methoxy-pyrimidine.

(B) bringing this compound, suspended in dimethylformamide, into contact with thionyl chloride, at room temperature, in order to form the corresponding 4-chloro-5-alkoxycarbonyl-2-methoxy-pyrimidine:

The invention is described in the non-limiting examples which follow.

EXAMPLE 1

4-Chloro-5-ethoxycarbonyl-2-methoxy-pyrimidine

Stage A — 5-Ethoxycarbonyl-4-hydroxy-2-methoxy-2-pyrimidine 324 g (1.5 mol) of ethyl ethoxymethylenemalonate are added to a solution of 185 g (0.75 mol) of the neutral sulphate of O-methylisourea in 2.25 of water, which is kept stirring vigorously. A solution of 120 g (3 mols) of sodium hydroxide in 750 cm$^3$ of water is added slowly, with continuous stirring, to the suspension thus obtained. During the addition of the akaline reagent (duration: about 1 hour 30 minutes), the sodium salt of 5-ethoxycarbonyl-4-hydroxy-2-methoxy-pyrimidine precipitates. The thick mass is again stirred for 2 hours at room temperature.

Whilst maintaining the stirring, the pH of the medium is adjusted to 5, by the addition of acetic acid. The precipitate passes into solution. A small quantity of gelatinous insoluble matter is filtered off in the presence of diatomaceous earth.

The limpid solution is extracted with chloroform (1.25 l). The organic phase is decanted off, washed with water and dried (MgSO$_4$).

By evaporation of the solvent in vacuo, 229 g (yield 77%) of 5-ethoxycarbonyl-4-hydroxy-2-methoxy-pyrimidine are obtained which are purified by recrystallisation from isopropanol; melting point 146° C.

Analysis for $C_8H_{10}N_2O_4$ (molecular weight 198.18): % calculated: C, 48.48; H, 5.09; N, 14.14. % found: C, 48.51; H, 5.10; N, 13.90.

Stage B — 4-Chloro-5-ethoxycarbonyl-2-methoxy-pyrimidine 99 g (0.5 mol) of 5-ethoxycarbonyl-4-hydroxy-2-methoxy-pyrimidine are suspended in 200 cm$^3$ of dimethylformamide (D.M.F.). 89 g (0.75 mol) of thionyl chloride are added, over a period of about 5 minutes, to the mixture which is stirred. The solid material passes into solution with heating. The homogeneous solution is stirred again for 30 minutes at ambient temperature.

The mixture is poured slowly, with stirring, into a mixture of ice (250 g) and water (1 liter). After further stirring (15 minutes), the product of the reaction is extracted with 2 × 400 cm$^3$ of benzene. The combined extracts are washed with a dilute sodium bicarbonate solution and then with water, and dried (MgSO$_4$). By concentration in vacuo, 4-chloro-5-ethoxycarbonyl-2-methoxy-pyrimidine is obtained, in the form of an oil, weighing 101.6 g (yield 94%).

The product is purified by distillation in vacuo, boiling point$_{0.9}$ = 120° C; the distillate crystallises and has a melting point of 26°-28° C.

Analysis for $C_8H_9ClN_2O_3$ (molecular weight 216.5): % calculated: C,44.34; H,4.16; N,12.93. % found: C,44.18; H,4.33; N,12.88.

EXAMPLE 2

6-Ethoxycarbonyl-8-ethyl-2-methoxy-5-oxo-5,8-dihydro-pyrido[2,3-d]pyrimidine

Stage C 101.6 g (0.47 mol) of 4-chloro-5-ethoxycarbonyl-2-methoxy-pyrimidine, obtained as in Example 1, are dissolved in 500 cm$^3$ of benzene and 51 g (0.5 mol) of triethylamine. The mixture is stirred and cooled externally by a water bath. 73 g (0.5 mol) of ethyl N-ethyl-β-aminopropionate are slowly added thereto (duration of the addition: 45 minutes); the temperature of the medium rises from 20° C to 49° C. The reaction is completed by heating, for 2 hours at 50° C. After cooling, the mixture is washed with 2 × 500 cm$^3$ of water. The organic phase is dried (MgSO$_4$). Evaporation of the solvent leaves 4-(N-ethyl-N-β-ethoxycarbonylethyl)-amino-5-ethoxycarbonyl-2-methoxy-pyrimidine in the form of an oil. Quantitative yield: 152.3 g.

Stage D 12.6 g of sodium are dissolved in 500 cm$^3$ of absolute ethanol. The excess solvent is driven off in vacuo at 50° C in an atmosphere of dry nitrogen. The remaining sodium ethylate is dissolved in 250 cm$^3$ of D.M.F. and the solution is stirred. A solution of 152 g (0.47 mol) of 4-(N-ethyl-N-β-ethoxycarbonylethyl)-amino-5-ethoxycarbonyl-2-methoxy-pyrimidine in 160 cm$^3$ of D.M.F. is added thereto at room temperature. During the addition (about 15 minutes), the mixture is cooled externally, so as to keep the temperature of the reaction mixture between 20° and 25° C. The mixture is stirred for 1 hour at room temperature and then heated for 1 hour at 50° C in vacuo (15 mm) in order to remove the ethanol formed in the reaction.

After cooling, the mixture is cooled (sic) using a bath of iced water, and 33 g (0.55 mol) of acetic acid and then 2 l of water are added thereto. During these operations, care is taken that the temperature of the medium remains between 15° and 25° C.

The reaction product which precipitates is filtered off, washed with water and dried; 113.6 g (yield 87%) of 6-ethoxycarbonyl-8-ethyl-2-methoxy-5-oxo-5,6,7,8-tetrahydropyrido[2,3-d]pyrimidine are obtained which is purified by recrystallisation from ethanol and then has a melting point of 118° C.

Analysis for $C_{13}H_{17}N_3O_4$ (molecular weight 279.29): % calculated: C,55.90; H,6.14; N,15.05. % found: C,56.24; H,6.28; N,14.80.

Stage E 102 g (0.366 mol) of 6-ethoxycarbonyl-8-ethyl-2-methoxy-5-oxo-5,6,7,8-tetrahydro-pyrido[2,3-d]pyrimidine and 37 g (0.366 mol) of triethylamine are dissolved in 750 cm³ of chloroform. The mixture is stirred at room temperature and a solution of 80 g of bromine in 350 cm³ of chloroform is added thereto (duration of the addition: 1 hour 30 minutes). The mixture is stirred again for 1 hour at ambient temperature and a major portion of the solvent is driven off in vacuo. The residue is taken up in 550 cm³ of ethanol, the solution is stirred and a solution of 74 g (0.732 mol) of triethylamine in 100 cm³ of ethanol is poured therein, over a period of 15 minutes. The reaction is exothermic and the reaction product crystallises from the medium at the end of the addition of the triethylamine.

The mixture is heated, with stirring, so as to distil off the residual chloroform, and is then heated under reflux for 30 minutes. The solvent is driven off in vacuo. After cooling, the residue is taken up in 500 cm³ of water. The precipitate is filtered off, washed with water and dried in vacuo. 92 g (yield 90.5%) of crude 6-ethoxycarbonyl-8-ethyl-2-methoxy-5-oxo-5,8-dihydropyrido[2,3-d]pyrimidine is obtained, which has a melting point of 149° C and which, after recrystallisation from 650 cm³ of methanol, gives 81.3 g (yield 80%) of the pure product, which has a melting point of 152° C and which is identical to the product described in the literature.

Analysis for $C_{13}H_{15}N_3O_4$ (molecular weight 277.27): % calculated: C,56.31; H,5.45; N,15.16. % found: C,56.19; H,5.58; N,14.90.

Examples 3 and 4 which follow are given in order to illustrate the preparation of two antibacterial agents, namely pyromidic acid and pipemidic acid, starting from the product of Example 2.

EXAMPLE 3

2-Pyrrolidino-5-oxo-8-ethyl-5,8-dihydro-pyrido[2,3-d]pyrimidine-6-carboxylic acid 5.9 g of 6-ethoxycarbonyl-8-ethyl-2-methoxy-5-oxo-5,8-dihydro-pyrido[2,3-d]pyrimidine, 4.6 g. of pyrrolidine and 12 g of toluene are heated for 2 hours at 90° C. After cooling, 100 cm³ of water are added to the mixture. The precipitate is filtered off and washed with water. After drying, 5.5 g of 6-ethoxycarbonyl-8-ethyl-5-oxo-2-pyrrolidino-5,8-dihydro-pyrido[2,3-d]pyrimidine are obtained. After recrystallisation from ethanol, it melts at 202° C and is identical to the product described in the literature.

Saponification of this ester (5.5 g) under reflux in an alkaline solution (NaOH: 0.8 g / water: 40 cm³) gives, after acidification, the corresponding acid (pyromidic acid, melting point 322° C), which is identical to the product described in the literature.

EXAMPLE 4

2-Piperazinyl-5-oxo-8-ethyl-5,8-dihydro-pyrido[2,3-d]pyrimidine-6-carboxylic acid 23 g (0.12 mol) of piperazine hexahydrate are heated at 80° C in a flask. The molten mixture is stirred and 11.1 g (0.04 mol) of 6-ethoxycarbonyl-8-ethyl-2-methoxy-5-oxo-5,8-dihydro-pyrido[2,3-d]pyrimidine are added thereto. The stirring and the temperature are maintained for one hour. After cooling, the mixture is taken up in 50 cm³ of water and a solution of 1.8 g of sodium hydroxide in 40 cm³ of water is added thereto. The mixture is stirred for 3 hours at room temperature. A small quantity of insoluble matter is filtered off. The solution is adjusted to pH 6.5 by the addition of acetic acid. The precipitate is filtered off and washed with water. The precipitate is dissolved in a solution of acetic acid (10 cm³) in water (50 cm³) in order to purify it. Animal charcoal (1 g) is added to the slightly cloudy solution, which is stirred and then filtered. The solution is adjusted to pH 7 by the addition of 20% strength sodium hydroxide, with stirring.

The precipitate formed is filtered off, washed with water and then with ethanol and dried at 100° C in vacuo. 10.4 g (yield 86%) of 8-ethyl-5-oxo-2-piperazinyl-5,8-dihydro-pyrido[2,3-d]pyrimidine-6-carboxylic acid (pipemidic acid), having a melting point of 264° C, are thus obtained, this being identical to the product described in the literature.

We claim:

1. Process for the preparation of a 4-chloro-5-alkoxycarbonyl-2-methoxy-pyrimidine of the formula:

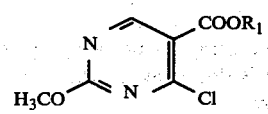

in which $R_1$ is alkyl of 1 to 4 carbon atoms, which comprises:

(A) condensation of a salt of O-methylisourea and an inorganic or organic acid, with an alkyl alkoxymethylene-malonate

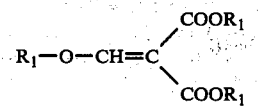

in an aqueous medium and in the presence of an excess of an alkali metal hydroxide, to form the corresponding salt of the 5-alkoxycarbonyl-4-hydroxy-2-methoxy-pyrimidine, and neutralisation of the said salt by the addition of an inorganic or organic acid in order to liberate this 5-alkoxycarbonyl-4-hydroxy-2-methoxy-pyrimidine of formula:

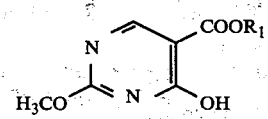

and (B) bringing this compound, suspended in dimethylformamide, into contact with thionyl chloride, at room temperature, in order to form the corresponding 4-chloro-5-alkoxycarbonyl-2-methoxy-pyrimidine of formula:

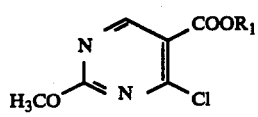

2. Process according to claim 1 which comprises the following stages:
  (A) condensation of a salt of O-methylisourea and an inorganic or organic acid, with ethyl ethoxymethylenemalonate, in an aqueous medium and in the presence of an excess of an alkali metal hydroxide, to form the corresponding salt of 5-ethoxycarbonyl-4-hydroxy-2-methoxy-primidine, followed by neutralisation of the salt formed, by the addition of an inorganic or organic acid, in order to liberate 5-ethoxycarbonyl-4-hydroxy-2-methoxy-pyrimidine, which is isolated, and
  (B) bringing the hydroxy derivative thus obtained, suspended in dimethylformamide, in contact with thionyl chloride, at room temperature, in order to form the desired 4-chloro-5-ethoxycarbonyl-2-methoxy-pyrimidine.

3. Process according to claim 2, in which the salt of O-methylisourea is the neutral sulphate of O-methylisourea, which is used in the ratio of 1 mol of neutral sulphate for 2 mols of ethyl ethoxymethylenemalonate.

4. Process according to claim 1, in which thionyl chloride is used in stage B in the ratio of at least 1 mol per mol of hydroxy-derivative.

* * * * *